United States Patent
Palermo et al.

(10) Patent No.: US 11,918,020 B2
(45) Date of Patent: Mar. 5, 2024

(54) FOOD PRODUCT COMPRISING A CO-CULTURE OF BACTERIA AND FUNGI

(71) Applicant: AquaCultured Foods, Inc., Chicago, IL (US)

(72) Inventors: Anne Palermo, Barrington, IL (US); Robert Schultz, Chicago, IL (US)

(73) Assignee: AquaCultured Foods, Inc., Chicago, IL (US)

( * ) Notice: Subject to any disclaimer, the term of this patent is extended or adjusted under 35 U.S.C. 154(b) by 0 days.

(21) Appl. No.: 18/199,911

(22) Filed: May 19, 2023

(65) Prior Publication Data

US 2023/0284669 A1    Sep. 14, 2023

Related U.S. Application Data

(63) Continuation of application No. PCT/US2022/029353, filed on May 14, 2022.
(Continued)

(51) Int. Cl.
*A23L 33/195* (2016.01)
*A23J 3/20* (2006.01)
(Continued)

(52) U.S. Cl.
CPC ............. *A23L 33/195* (2016.08); *A23J 3/20* (2013.01); *A23L 31/10* (2016.08); *A23L 33/135* (2016.08)

(58) Field of Classification Search
CPC ...... A23L 33/195; A23L 31/10; A23L 33/135; A23J 3/20
(Continued)

(56) References Cited

U.S. PATENT DOCUMENTS 6,936,463 B1   8/2005 Chen et al.
7,235,276 B2   6/2007 Allen et al.
(Continued)

FOREIGN PATENT DOCUMENTS

CN    109566758 A    4/2019
EP    1555999 B1    8/2012
(Continued)

OTHER PUBLICATIONS

Harrison, et al. Microbial composition of SCOBY Starter Cultures Used by Commercial Kombucha Brewers in North America, Microorganisms, vol. 9, No. 1060, May 14, 2021.
(Continued)

*Primary Examiner* — Hamid R Badr
(74) *Attorney, Agent, or Firm* — Cooley LLP

(57) ABSTRACT

Provided herein is a composition comprising a solid product of a co-culture of bacteria and fungi, comprising at least 5% protein by dry weight and at least 5% fiber by dry weight. Further provided is a food article formed from a pellicle comprising a solid product of a co-culture of bacteria and fungi, which comprises at least 5% fungal protein by dry weight and at least 5% fiber by dry weight, and which is formed into a shape by cutting or molding. Further provided is a method of making such products by co-culturing bacteria and fungi to form a pellicle, and harvesting and shaping the pellicle. Further provided is a system that optimizes growth and production of a co-culture of bacteria and fungi (co-culture of microorganism) that includes a housing unit that includes stacked trays.

30 Claims, 7 Drawing Sheets

Related U.S. Application Data

(60) Provisional application No. 63/267,191, filed on Jan. 26, 2022, provisional application No. 63/244,821, filed on Sep. 16, 2021, provisional application No. 63/189,314, filed on May 17, 2021.

(51) Int. Cl.
*A23L 31/10* (2016.01)
*A23L 33/135* (2016.01)

(58) Field of Classification Search
USPC .......................................................... 426/52
See application file for complete search history.

(56) References Cited

U.S. PATENT DOCUMENTS

| | | | |
|---|---|---|---|
| 7,811,795 B2 | 10/2010 | Delaquis | |
| 8,877,498 B2 | 11/2014 | Wegst et al. | |
| 9,096,836 B2 | 8/2015 | Wood et al. | |
| 9,175,153 B2 | 11/2015 | Trexler et al. | |
| 9,469,838 B2 | 10/2016 | Schaak et al. | |
| 9,532,589 B2 | 1/2017 | Skripitsyna | |
| 9,611,495 B2 | 4/2017 | Tajima et al. | |
| 9,657,279 B2 | 5/2017 | Voigt et al. | |
| 10,435,665 B2 | 10/2019 | Gerard et al. | |
| 10,596,209 B2 | 3/2020 | Toledo et al. | |
| 10,787,634 B2 | 9/2020 | Tull et al. | |
| 10,933,579 B2 | 3/2021 | Matheu | |
| 11,033,050 B2 | 6/2021 | Moshasha et al. | |
| 11,058,137 B2 * | 7/2021 | Pattillo ................... | C12N 1/14 |
| 2008/0096265 A1 | 4/2008 | Panchaud-Mirabel | |
| 2009/0010976 A1 | 1/2009 | Lintner | |
| 2010/0203581 A1 | 8/2010 | Morinaga et al. | |
| 2017/0313973 A1 | 11/2017 | Guzzo et al. | |
| 2018/0258454 A1 | 9/2018 | Buechter | |
| 2018/0355393 A1 | 12/2018 | Schwarz et al. | |
| 2019/0174815 A1 * | 6/2019 | Moshasha ............... | A24D 1/002 |
| 2020/0131096 A1 | 4/2020 | Kanagalingam et al. | |
| 2020/0216797 A1 | 7/2020 | Dyson et al. | |
| 2020/0221728 A1 | 7/2020 | Shigeta et al. | |
| 2020/0260760 A1 | 8/2020 | Houle et al. | |
| 2020/0270559 A1 | 8/2020 | Macur et al. | |
| 2020/0353130 A1 | 11/2020 | Ulmer | |
| 2020/0392668 A1 | 12/2020 | Ouzounov et al. | |
| 2021/0030818 A1 | 2/2021 | Ghannoum | |
| 2021/0115483 A1 | 4/2021 | Coburn et al. | |
| 2021/0220396 A1 | 7/2021 | Wolfe et al. | |
| 2021/0301471 A1 | 9/2021 | Moshasha et al. | |
| 2022/0088270 A1 | 3/2022 | Frey et al. | |
| 2022/0106459 A1 | 4/2022 | Dourado et al. | |
| 2022/0220521 A1 | 7/2022 | Terrell et al. | |

FOREIGN PATENT DOCUMENTS

| | | |
|---|---|---|
| EP | 3967748 A1 | 3/2022 |
| KR | 101797813 B1 | 11/2017 |
| RU | 2624242 C1 | 7/2017 |
| RU | 2647458 C1 | 3/2018 |
| RU | 2706726 C1 | 11/2019 |
| WO | 2019039973 A1 | 2/2019 |
| WO | 2019154849 A1 | 8/2019 |
| WO | WO-2021035115 A2 | 2/2021 |
| WO | 2022003100 A1 | 1/2022 |
| WO | 2022034092 A1 | 2/2022 |
| WO | WO-2022245683 A2 | 11/2022 |

OTHER PUBLICATIONS

International Search Report and Written Opinion for PCT/US2022/029353 dated Jan. 5, 2023, 21 pages.
Kozyrovska et al., "Kombucha microbiome as a probiotic: a view from the perspective of post-genomics and synthetic ecology," Biopolymers and Cell, Dec. 31, 2012. vol. 28, No. 2 pp. 103-113.
Berglund et al., "Wood hemicelluloses exert distinct biomechanical contributions to cellulose fibrillar networks". Nature Communications. Sep. 17, 2020; 11(1): pp. 1-16.
Lopez-Sanchez et al., "Cellulose-pectin composite hydrogels: Intermolecular interactions and material properties depend on order of assembly". Carbohydrate polymers. Apr. 15, 2017; 162: 71-81.
Lopez-Sanchez et al., "Pectin impacts cellulose fibre architecture and hydrogel mechanics in the absence of calcium". Carbohydrate Polymers. Nov. 20, 2016;153:236-45.
Rahardjo et al., "Contribution of aerial hyphae of Aspergillus oryzae to respiration in a model solid-state fermentation system". Biotechnology and Bioengineering. Jun. 5, 2002; 78(5): 539-44.
De Oliveira et al., Bacterial cellulose membranes constitute biocompatible biomaterials for mesenchymal and induced pluripotent stem cell culture and tissue engineering. J Tissue Sci Eng. S. 2012;11: pp. 1-4.
Hu et al., "Effects of pullulan additive and co-culture of Aureobasidium pullulans on bacterial cellulose produced by Komagataeibacter hansenii". Bioprocess and biosystems engineering. Mar. 2022 ;45(3): 573-87.
International Preliminary Report on Patentability for International Application No. PCT/US2022/029353 dated Nov. 30, 2023, 17 pages.
Invitation to pay additional fees for International Application No. PCT/US2023/025634, dated Nov. 21, 2023, 23 pages.
Rambo et al., "Template assisted synthesis of porous nanofibrous cellulose membranes for tissue engineering". Materials Science and Engineering: C. May 1, 2008; 28(4): 549-54.

* cited by examiner

Fig. 4
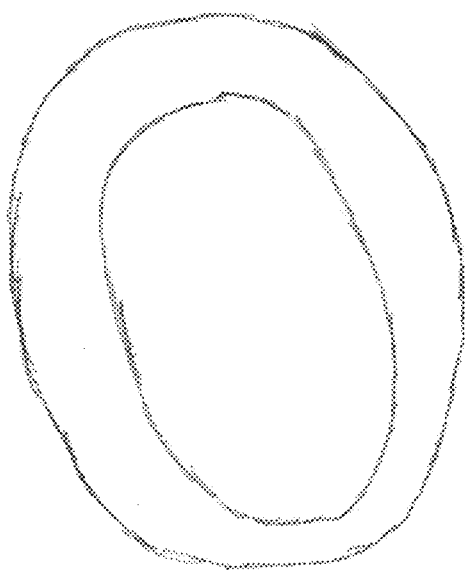
4D
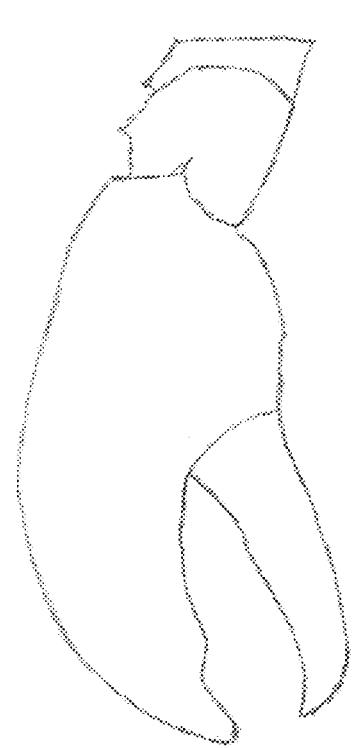
4E
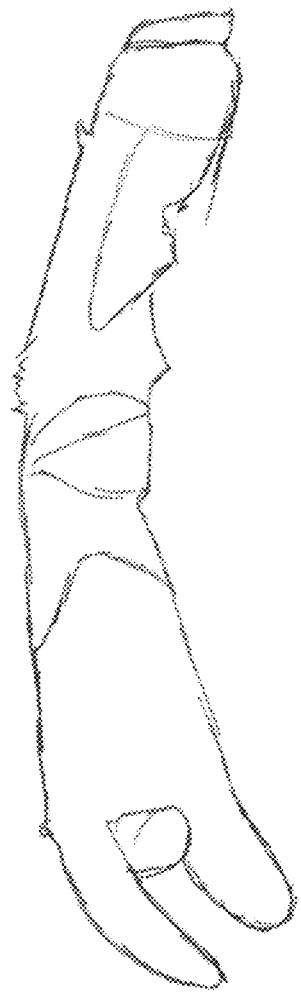
4F
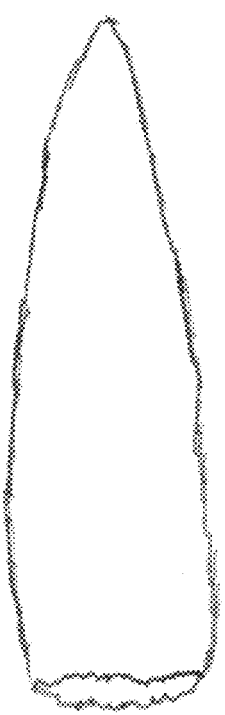
4G

Fig. 4
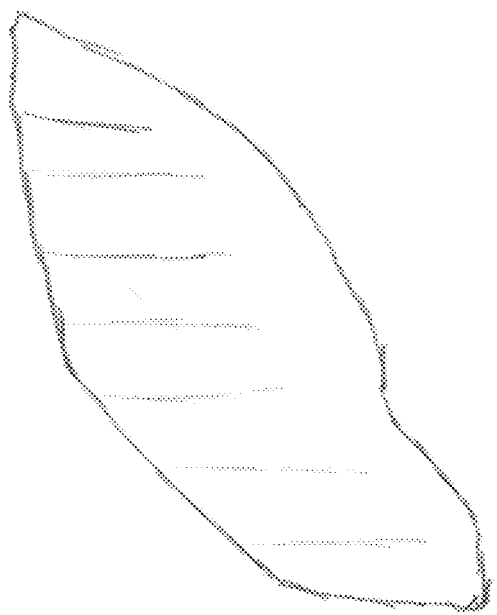
4I
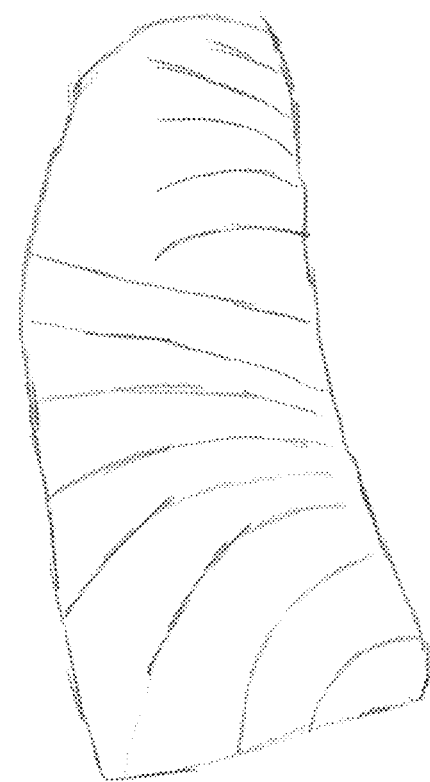
4H
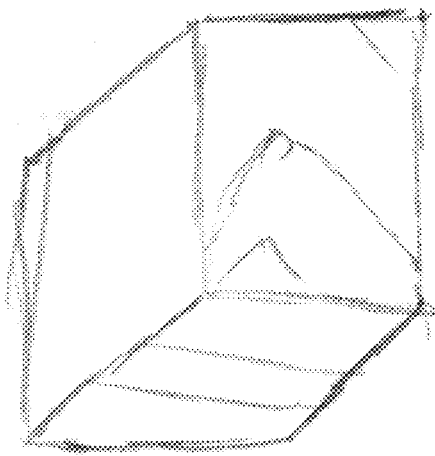
4J

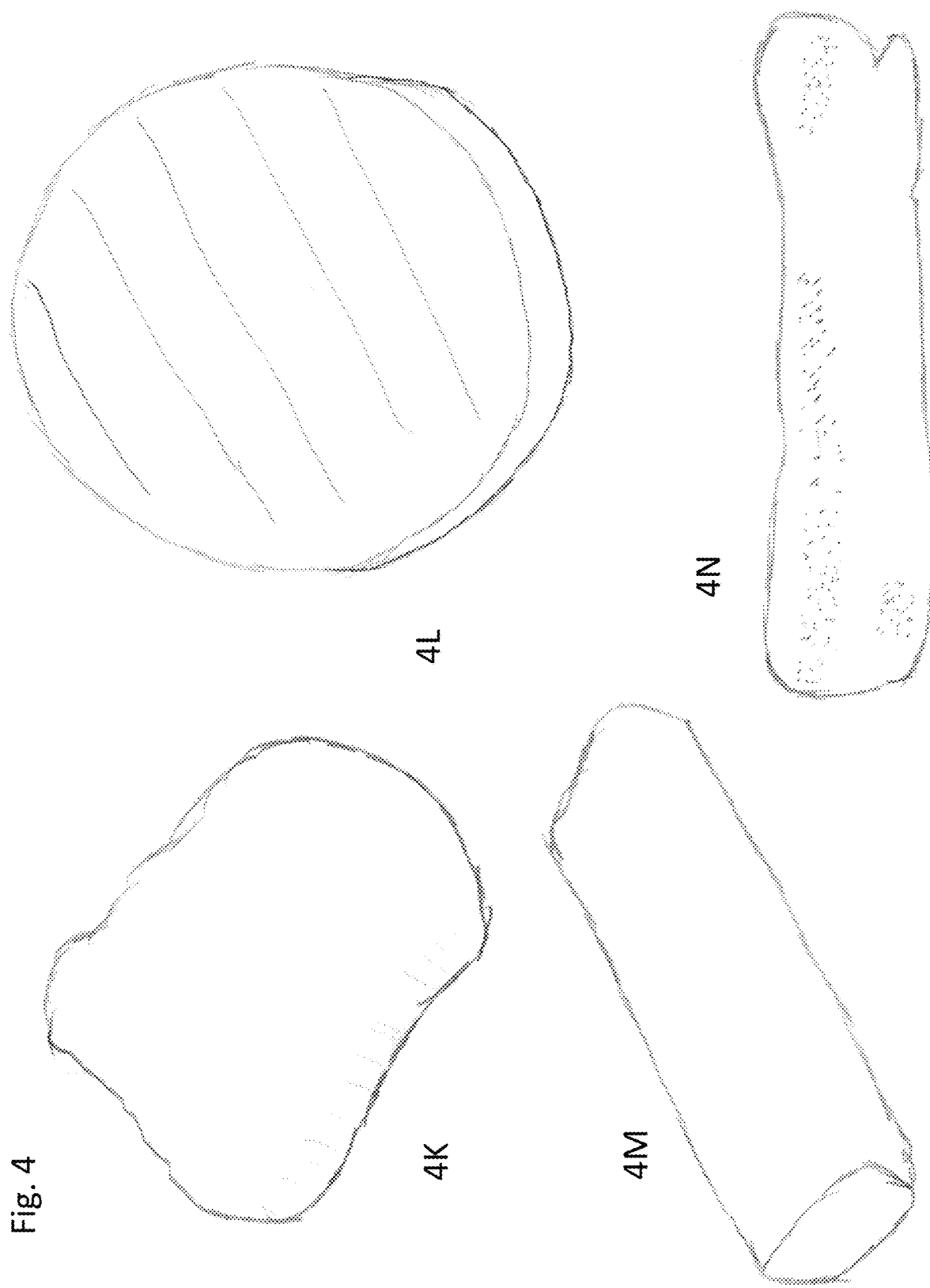

FOOD PRODUCT COMPRISING A CO-CULTURE OF BACTERIA AND FUNGI

REFERENCE TO RELATED APPLICATIONS

This application is a continuation of and claims priority to International Patent Application No. PCT/US2022/029353, filed May 14, 2022, which claims the benefit, under 35 U.S.C. § 119(e)(1), of the priority date of U.S. Provisional Patent Applications 63/189,314, filed May 17, 2021; 63/244,821, filed Sep. 16, 2021; and 63/267,191, filed Jan. 26, 2022, the contents of which are incorporated herein by reference in their entireties.

STATEMENT AS TO FEDERALLY SPONSORED RESEARCH

None.

BACKGROUND

The field of the invention and its embodiments relate to bioengineering and optimization of growth and production of a consortium of microorganisms including fungi, yeasts, algae and/or bacteria for use within the food industry.

However, what is needed is a novel system and method for optimizing the growth and production of these components to create a product usable in the food industry, such as a food source, a protein source, or its use in applications of plant protein products, including meat, seafood, and poultry analogues.

The means of operation of various systems disclosed herein are substantially different from existing methods, thereby solving problems associated with the existing methods.

In order to provide alternatives to animal-based products, including meats and seafood, the food industry is developing animal-free or animal reduced food products that mimic the taste and texture of natural animal-based products.

BRIEF DESCRIPTION OF THE DRAWINGS

The accompanying drawings, which are incorporated herein and form a part of the specification, illustrate exemplary embodiments and, together with the description, further serve to enable a person skilled in the pertinent art to make and use these embodiments and others that will be apparent to those skilled in the art. The invention will be more particularly described in conjunction with the following drawings wherein.

SUMMARY

Figure 1:
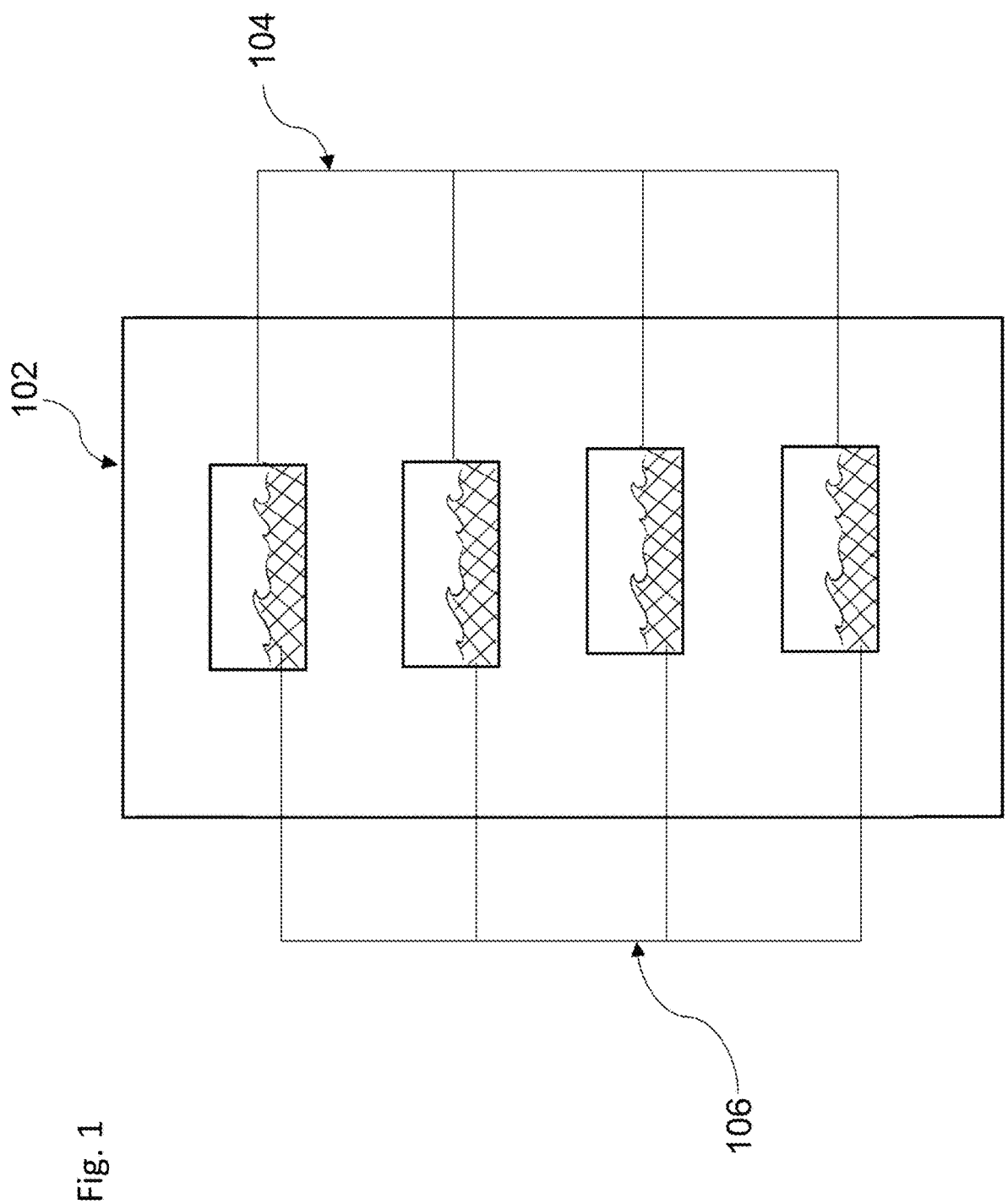
FIG. 1 depicts a system configured to optimize a growth and a production of a co-culture of a bacterium and a fungus, according to at least some embodiments disclosed herein.

Provided herein are food products, compositions and articles. The foods comprise a scaffold of cellulose, typically bacterial cellulose, in which cells, such as fungi and bacteria, are embedded. The compositions comprise at least 5% protein and at least 5% fiber by dry weight. The foods comprise fungi and, typically, bacteria. The compositions can be produced as a co-culture, e.g., a symbiotic co-culture, of fungi and bacteria. Such a co-culture produces a pellicle, which can be shaped into articles to mimic food shapes or geometric or fanciful designs.

The present invention and its embodiments relate to bioengineering and optimization of the growth and the production of a consortium of microorganisms including fungi, yeasts, algae and/or bacteria for use within the food industry. In particular, the present invention and its embodiments relate to a system that optimizes growth and production of a symbiotic co-culture of fungi and cellulose-producing bacteria, in which the product of the co-culture comprises a protein source, and/or its use in applications of alternative protein products and plant protein products, including meat, seafood and poultry analogues.

An embodiment of the present invention describes a system configured to optimize the growth and the production of a symbiotic co-culture of bacteria and fungi. The system includes a housing unit. The housing unit includes stacked trays that house a culture medium (also called a seed liquid) inoculated with bacteria and fungi. The seed liquid is a prepared broth comprising a feedstock. The feedstock may comprise a carbon source (e.g., one or more sugars), a nitrogen source, and additional nutrients.

The fungus can be, for example, *Medusomyces gisevii* Lindau. The product of the co-culture can be used, for example, in a food application. In preferred examples, the product of the co-culture is used as a food source, a protein source, or is used in applications of plant protein products, including meat, seafood and poultry analogues.

In examples, the fermentation culture comprises fungi (e.g., *Aspergillus* or a yeast), bacteria, nutrients, probiotics, microbes, a vinegar by-product of an aerobic digestion of a carbon source and nitrogen, and/or prebiotics, among other components not explicitly listed herein. In some examples, the strain of the bacteria comprises a genus of *Acetobacter, Komagataeibacter* or *Gluconacetobacter*. In other examples, the fermentation culture comprises a biomass material configured to accelerate growth of the symbiotic co-culture.

In certain embodiments the microbes in the co-culture comprise or consist of a bacterium and a fungus as set forth in Table 1:

TABLE 1

| Bacterium/Fungus Combinations |
| --- |
| *Komagataeibacter xylinus* and *Aspergillus oryzae* |
| *Komagataeibacter hansensii* and *A. oryzae* |
| *Komagataeibacter rhaeticus* and *A. oryzae* |
| *Komagataeibacter xylinus* and *Neurospora crassa* |
| *Komagataeibacter xylinus* and *Neurospora intermedius* |
| *Komagataeibacter hansensii* and *Neurospora crassa* |
| *Komagataeibacter hansensii* and *Neurospora intermedius* |
| *Komagataeibacter rhaeticus* and *Neurospora crassa* |
| *Komagataeibacter rhaeticus* and *Neurospora intermediius* |
| *Komagataeibacter xylinus* and *Fusarium venenatum* |
| *Komagataeibacter xylinus* and *Fusarium venenatum* |
| *Komagataeibacter hansensii* and *Fusarium venenatum* |
| *Komagataeibacter hansensii* and *Fusarium venenatum* |
| *Komagataeibacter rhaeticus* and *Fusarium venenatum* |

In the housing unit, each of the stacked trays can be loosely covered to reduce evaporation rate and to allow oxygen to flow to the seed liquid and the co-culture of microorganisms. A gap can exist between each tray to allow for heat, humidity and gas transfer between the trays. Further, the trays can be stacked vertically to allow for maintenance of a temperature between approximately 40° F. and approximately 122° F.; and/or for maintenance of a relative humidity of approximately 20-90% RH. In some examples, the preferred relative humidity is 90% RH.

In general, the present invention succeeds in conferring the following benefits and objectives.

It is an objective of the present invention to provide a system that optimizes growth and production of a co-culture of microorganisms, where the product of the co-culture is used as a food source, a protein source, or is used in applications of plant protein products/alternative protein, including meat, seafood and poultry analogues.

It is an objective of the present invention to provide a system that optimizes the growth and the production of a consortium of microorganisms including fungi, yeasts, and bacteria for use within the food industry.

It is an objective of the present invention to provide a method to grow and produce a microbe-based consortium of nutritional fungi and bacteria to be used as a nutrient rich food source with high levels of protein, dietary fibers, and micronutrients.

It is an objective of the present invention to provide a food product derived from a co-culture of microorganisms, which food product is high in protein and fiber.

DETAILED DESCRIPTION

I. Introduction

The preferred embodiments of the present invention will now be described with reference to the drawings. Identical elements in the various figures are identified with the same reference numerals. Reference will now be made in detail to each embodiment of the present invention. Such embodiments are provided by way of explanation of the present invention, which is not intended to be limited thereto. In fact, those of ordinary skill in the art will appreciate upon reading the present specification and viewing the present drawings that various modifications and variations can be made thereto.

Provided herein is a food product comprising a co-culture of bacteria and fungi (also referred to as a "co-culture of microorganisms") comprising at least 5% protein and 5% fiber by dry weight, as well as methods and systems for making such a food product.

II. Methods of Making a Food Product Comprising a Co-Culture of Bacteria and Fungi A co-culture of microorganisms is formed as a pellicle floating on a fermentation culture. Methods of making a pellicle comprising a co-culture of microorganisms can begin with combining, in a fermentation vessel, a starter culture and a culture medium (or seed liquid), to produce a fermentation culture. The fermentation culture is fermented for a time sufficient to produce a pellicle. After it is produced, the pellicle is harvested, typically for further processing.

A. Fermentation Culture

A fermentation culture can comprise a starter culture and a culture medium. A high-protein product can be produced by including in the culture one or more fungi (e.g., yeast) that is not a strong fermenter and/or adding to the culture medium an organic nitrogen source in an amount of at least 5 grams per liter, e.g., at least 7.5 grams per liter, at least 10 grams per liter or at least 15 grams per liter.

High-protein products can be produced by including in the culture one or more fungi in a batch reactor or a semi-batch reactor. One or more fungi in the starter culture may have a volume that is greater than or equal to about 0.1%, 0.5%, 1%, 2%, 4%, 6%, 8%, 10%, 15%, 20%, 25%, or greater, of the volume of the reactor.

The starter culture may be added to the reactor during the exponential growth phase of the starter culture. The exponential growth phase may be detected by the optical density (OD) of the starter culture. The OD of the exponential growth phase may be culture specific and also may vary for fungal or bacterial cultures. The wavelength used to detect the OD of the starter culture may be greater than or equal to about 400 nanometers (nm), 450 nm, 500 nm, 550 nm, 600 nm, 650 nm, 700 nm, or more. The starter culture may be added to the reactor when the OD is greater than or equal to 0.1, 0.2, 0.3, 0.4, 0.5, 0.6, 0.7, 0.8, 0.9, 1.0, 1.2, 1.5, or more.

The fermentation culture can be free of, or contain no more than miniscule or trace amounts of, an agricultural substrate such as corn stalks, silage or straw of grass crops, including maize, sorghum, rye, wheat, or oats, such that a majority, 75%, 90% or 95% of the fungi are not growing on the agricultural substrate.

1. Culture Medium

The culture medium can comprise water, a carbon source, a nitrogen source (organic or inorganic), and nutrients. The carbon source can be present at a concentration of, for example, at least any of 10 grams/liter, 20 grams/liter, 30 grams/liter, 40 grams/liter, 50 grams/liter, 60 grams/liter, 70 grams/liter, 80 grams/liter, 90 grams/liter, or 100 grams/liter. The nitrogen source can be present at a concentration of, for example, at least any of 1 gram/liter, 2 grams/liter, 3 grams/liter, 4 grams/liter, 5 grams/liter, 6 grams/liter, 7 grams/liter, 8 grams/liter, 9 grams/liter, 10 grams/liter, 11 grams/liter, 12 grams/liter, 13 grams/liter, 14 grams/liter, or 15 grams/liter.

The carbon source can comprise a sugar, such as glucose, fructose, sucrose, lactose, galactose, maltose, trehalose, allulose, or maltotriose. The sugar can comprise a refined sugar, a purified sugar, or a crude sugar. The carbon source can comprise honey. The carbon source can comprise a polyol, such as glycerol, erythritol, starch hydrolysates, isomalt, lactitol, maltitol, mannitol, sorbitol, or xylitol. The carbon source can comprise xanthan, agar, alginate, or konjac glucomannan. The carbon source can be an alcohol, such as ethanol or methanol.

An organic nitrogen source can comprise amino acids or nucleotides, or compounds comprising them, such as polymers, such as peptides, polypeptides, oligonucleotides, and nucleic acids. In addition, an organic nitrogen source can comprise any one or more of: a yeast extract, a peptone, a hydrolyzed corn protein, a hydrolyzed soy protein, a hydrolyzed pea protein. Certain agricultural byproducts containing high amounts of nitrogen can be used as an organic nitrogen source, such as corn steep liquor.

An inorganic nitrogen source can comprise any one or more of: a nitrate salt, a nitrite salt, an ammonia salt, a urea compound, nitrogen gas, and ammonium hydroxide. A nitrogen source can comprise any one or more of: a nitrate salt, an ammonia salt, a urea compound, nitrogen gas, and ammonium hydroxide.

Nutrients can comprise any one or more of: biotin, magnesium sulfate heptahydrate, calcium sulfate, zinc sulfate, ferric ammonium sulfate, copper sulfate, manganese sulfate, biotin, potassium hydrogen phosphate, disodium phosphate, ammonium nitrate, acetic acid and sodium acetate. Salts of calcium, magnesium, iron, zinc, copper and manganese can also be used as nutrients.

The culture medium can comprise, for example, Yamanaka medium or Hestrin-Schramm medium or modified versions thereof. For example, the culture medium can comprise 25 g/L glucose, 2.5 g/L ammonium sulfate, 2.5 g/L yeast extract and/or peptone, 1.5 g/L potassium hydrogen phosphate, 0.025 g/L magnesium sulfate heptahydrate. The pH of the culture medium can be adjusted to 3.5-7.0 using, e.g., sodium hydroxide, sodium acetate, sodium bicarbonate, acetic acid or hydrochloric acid. In certain embodiments animal peptone can be substituted with a plant-based soy- or pea-based peptone.

2. Starter Culture

Starter cultures used to make a co-culture of microorganisms comprise one or more fungi and one or more bacteria. Fungi are selected to, and are present in amounts that will, produce an ultimate product that is high in protein. Bacteria, which can produce cellulose (e.g., as part of an extracellular matrix), contribute fiber to the end product.

a) Fungi

Fungi are well suited for scaled food production because of their rapid rate of cell replication, aggressive digestion, colonization timing, adaptability, high protein production and ease of propagation. Many species of fungi are already accepted as safe in the human diet. Therefore, in one aspect, provided herein are food products containing fungi, which can be significantly higher in protein and fungal cells than are classic fermented foods that contain fungi.

Any fungus or combination of fungi can be used in the fermentation process. In various embodiments the number of different fungi used in the starter culture can be 1, 2, 3, 4, 5 or more than 5. Exemplary fungi typically belong to division Ascomycota (e.g., *Aspergillus*, yeast, *Fusarium*, *Penicillium*).

Exemplary fungi include those belonging to the divisions Chytridiomycota, Zygomycota (e.g. *Rhizopus oligosporus*), Basidiomycota, Deuteromycota or Glomeromycota.

In some embodiments the fungus can be any of *Aspergillus* (e.g., *Aspergillus oryzae*), *Fusarium* (e.g., *Fusarium venenatum*), tea fungus (e.g., *Medusomyces gisevii Lindau*), *Geotrichum* (e.g., *Geotrichum candidum*), *Penicillium* (e.g., *Penicillium camemberti* or *Penicillium roqueforti*), *Neurospora* (e.g., *Neurospora crassa*), *Paecilomyces* (e.g., *Paecilomyces variotii*) or *Rhizopus* (e.g., *Rhizopus oligosporus*). The fungus can be a filamentous fungus.

In some embodiments, the fungus is a yeast. Exemplary yeast include *Candida* (e.g., *Candida utilis*), *Rhodotorula* (e.g., *Rhodotorula mucilaginosa*), *Cyberlindnera* (e.g. *Cyberlindnera jadinii*), *Pichia* (e.g. *Pichia pastoris*) and *Saccharomyces* (e.g., *Saccharomyces cerevisiae*).

Exemplary fungi (e.g., yeasts) include those that proliferate in an acidic pH environment (i.e., pH less than 7), have a low flocculation rate and can grow within the extracellular matrix formed by the bacteria. For example, they flocculate late in the fermentation process, such as after 15 days.

In some embodiments, the fungus (e.g., the yeast) is not a strong fermenter (e.g., is not *Saccharomyces cerevisiae*). Fungi that are not strong fermenters do not appear dark (black or purple) or green when grown on eosin methylene blue (EMB) agar.

In certain embodiments, the concentration of fungi in the starter culture can be at least 1% of wet weight, at least 2% of wet weight, at least 3% of wet weight, at least 4% of wet weight, at least 5% of wet weight, or more.

b) Bacteria

Any bacterium or combination of bacteria can be used in the fermentation process. In various embodiments the number of different bacteria used in the starter culture can be 1, 2, 3, 4, 5 or more than 5.

In a preferred embodiment, the bacteria are cellulose-producing bacteria.

Exemplary bacteria include, for example, species of *Acetobacter*, *Bacillus*, *Bifidobacterium*, *Brachybacterium*, *Brevibacterium*, *Carnobacterium*, *Corynebacterium*, *Enterococcus*, *Gluconobacter*, *Gluconacetobacter*, *Corynebacterium*, *Halomonas*, *Komagataeibacter*, *Lactobacillus*, *Lactococcus*, *Leuconostoc*, *Macrococcus*, *Microbacterium*, *Micrococcus*, *Oenocuccus*, *Propionibacterium*, *Proteus*, *Pseudomonas*, *Psychrobacter*, *Streptococcus*, *Streptomyces*, *Tetragenococcus*, *Weissella* and *Zymomonas*.

In certain embodiments the starter culture comprises *Gluconacetobacter xylinus* and/or *Komagataeibacter rhaeticus*; and a fungus selected from one or more of *Candida utilis*, *Aspergillus oryzae*, *Cyberlindnera jadinii*, *Fusarium Venenatum* and *Rhizopus arrhizus*. The organisms may be selected or engineered for a high growth rate. Selection or engineering of the organism may include directed evolution, genetic engineering, or metabolic engineering.

In some embodiments, the culture is free of lactic acid bacteria, or contains less than 5%, less than 2% or less than 1% lactic acid bacteria to total bacteria by weight. Lactic acid bacteria comprise bacteria of the order Lactobacilliales. They include the genera *Lactobacillus*, *Leuconostoc*, *Pediococcus*, *Lactococcus*, and *Streptococcus*, *Aerococcus*, *Carnobacterium*, *Enterococcus*, *Oenococcus*, *Sporolactobacillus*, *Tetragenococcus*, *Vagococcus*, and *Weissella*.

In certain embodiments, the concentration of bacteria in the starter culture can be at least 1% of wet weight, at least 2% of wet weight, at least 3% of wet weight, at least 4% of wet weight, at least 5% of wet weight, or more.

B. Fermentation Culture Vessel

A fermentation culture is fermented in a fermentation vessel. The fermentation vessel used to produce a pellicle can have dimensions configured to produce a pellicle that can be shaped into a plurality of pieces of a desired size or shape. For example, such a pellicle can take the form of a slab which can be harvested from the surface of the fermentation vessel. Accordingly, the fermentation vessel can have a surface area between about 10 $cm^2$ and 5000 $cm^2$. For example, the fermentation vessel can have a surface area between about 100 $cm^2$ and about 1000 $cm^2$; or between about 200 $cm^2$ and about 600 $cm^2$; or about 400 $cm^2$. For example, the fermentation vessel can have a surface area of at least about any of 25 $cm^2$, 50 $cm^2$, 100 $cm^2$, 400 $cm^2$, 900 $cm^2$ and 5000 $cm^2$.

The surface area-to-volume ratio of the fermentation culture in the fermentation vessel also can be controlled to produce a pellicle of appropriate thickness. For example, the surface area:volume ratio can be greater than 1:6. For example, it can be between about 1:4 (e.g., a surface area of about 400 $cm^2$ and a volume of about 1600 $cm^3$) and about 1:6 (e.g., a surface area of about 400 $cm^2$ and a volume of about 2400 $cm^3$), e.g., about 1:3 (e.g., a surface area of about 400 $cm^2$ and a volume of about 1200 $cm^3$). In additional embodiments, the surface:volume ratio can be about 1:3 (e.g., a surface area of about 200 $cm^2$ and a volume of about 600 $cm^3$); 1:4 (e.g., a surface area of about 200 $cm^2$ and a volume of about 800 $cm^3$); 1:5 (e.g., a surface area of about 200 $cm^2$ and a volume of about 1,000 $cm^3$) or 1:6 (e.g., a surface area of about 200 $cm^2$ and a volume of about 1,200 $cm^3$).

C. Fermentation

Figure 3:
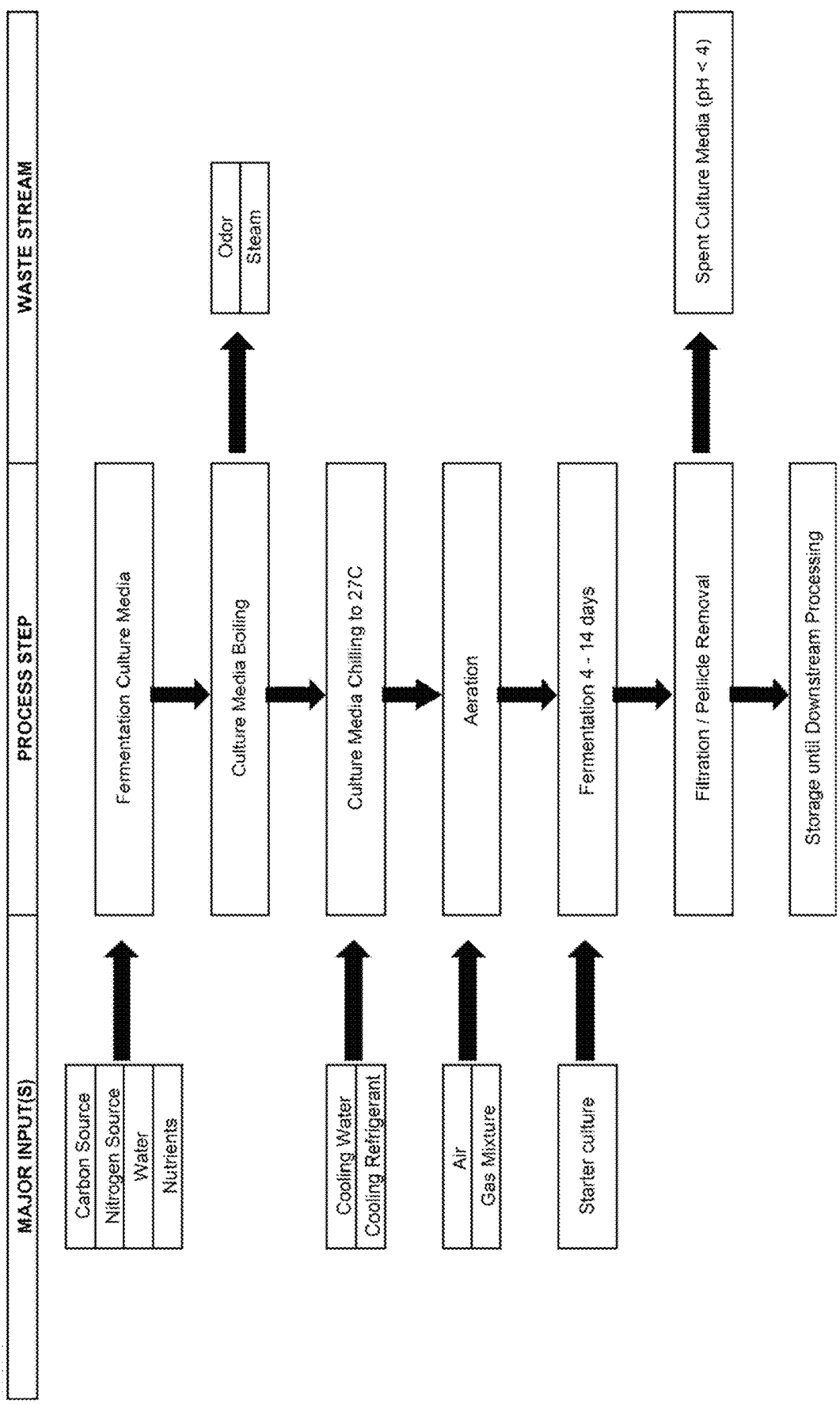
FIG. 3 depicts a flow chart of processes for making a pellicle comprising a co-culture of microorganisms.

Referring to FIG. 3, a fermentation culture medium comprising a carbon source, a nitrogen source, water and nutrients can be sterilized, e.g., by boiling or autoclaving. The culture medium can be cooled, e.g., to 27° C. Cooling can be performed with cooling water and/or cooling refrigerant. The medium can be aerated with air or other gas mixtures (i.e., containing oxygen). Starter culture is added to the culture medium, and the resulting fermentation culture is fermented for sufficient time to form a pellicle of desired thickness. After pellicle formation, the pellicle is removed from the spent culture medium. The pellicle can be washed and stored pending downstream processing.

Fermentation culture conditions influence the production of a pellicle from the co-culture. Culture conditions variables include, for example, temperature, pH, humidity, aeration and time.

1. pH

The fermentation culture can have a starting pH around 4.5, and it can be buffered to stay between pH 4.0 and pH 5.0, e.g., around 4.5. Fermentation at pH values outside of the aforementioned range result in lower growth rates of the microorganisms in the co-culture.

2. Temperature

The temperature of the fermentation culture can be maintained at between about 4° C. to about 50° C., e.g., about 25° C. to about 30° C. Maximal growth rates of the microorganisms in the co-culture are obtained at a temperature of about 30° C. Temperature can be controlled by controlling the ambient temperature of the room or housing unit, in which the culture is maintained.

3. Humidity

The humidity of the environment in which the culture is contained contributes to the moistness of the final product. Relative humidity can be maintained at about 20% and 90% RH. A preferred relative humidity is between about 40% and 60% RH, or about 50%. In additional embodiments, the relative humidity of the culture environment is about 90%.

4. Aeration

Proper aeration contributes to the growth of fungus. Methods of aerating the culture include the following. First, the culture vessel can be maintained open, or covered with a material that allows flow of air, such as cheesecloth or another porous material. Second, an air pump, for example an air stone or aeration wand, can be included in the fermentation vessel to provide air to the culture. An initial dissolved oxygen concentration of at least about 8 mg/L has positive effects. Dissolved oxygen can be between about 6 ppm to 10 ppm. Optimal oxygen concentration will depend on the fungal and bacterial constituents of the fermentation culture. An increased aeration rate can contribute to a pellicle product with a low cutting force.

5. Time

Once established according to the methods described herein, the culture can be fermented for about 4 to 30 days or more, e.g., between 5 days and 25 days, to produce a pellicle. For example, the culture can be fermented for at least any of 5 days, 10 days, 15 days, 20 days or 25 days. In some embodiments the culture is fermented for between four days and 14 days, or until a pellicle having a thickness of between 5 mm and 20 mm is produced. In certain embodiments, the fermentation mixture is fermented for any of about 1, 2, 3, 4, 5, 6, 7, 8, 9, 10, 15, 20, 25, 30 40, 50, 60 days.

D. Pellicle Formation, Harvest and Processing

The co-culture of bacteria and fungi in culture medium produces a solid product referred to as a "co-culture of microorganisms" or, if the fungus is yeast, a "symbiotic co-culture of bacteria and yeast" (also referred to by the acronym, "SCOBY"). The solid product forms as a pellicle on top of the fermentation culture. Pellicles produced by the methods described herein are characterized by a scaffold (e.g., an extracellular matrix) comprising bacterial cellulose and, optionally, other bacterial products such as protein. The pellicles further comprise bacterial and fungal cells, typically embedded in the scaffold. The cellulose can take to form of nanocellulose microfibrils. The product of fermentation of a co-culture of bacteria and fungi can be considered a biofilm or mat that houses the bacteria and fungal cultures.

Cultures can be configured to produce a pellicle having a thickness of at least about any of 1 mm, 2 mm, 5 mm, 1 cm, 2 cm, 3 cm, 4 cm, 5 cm, or 10 cm. In certain embodiments, the pellicle has a thickness between about 1 mm to 7.5 mm, between 10 mm and 25 mm, or between 2 mm and 50 mm.

Pellicles produced by the methods herein have a cutting force less than about 5 kg-force, e.g., less than 3 kg-force. This cutting force can be less than that of other products produced by, e.g., a SCOBY, resulting in a more tender product. Providing aeration to the culture contributes to a lower cutting force in the final product.

Crystallinity is a property of cellulose characterized by the relative abundance of ordered and amorphous cellulose as measured by x-ray crystallography, 13C NMR, Fourier Transform Infrared Spectroscopy and other methods. Crystallinity is given as a ratio. It can be calculated by dividing crystalline peak area by amorphous peak area. It is also referred to as crystallinity index. In certain embodiments of the compositions described herein, the crystallinity of the cellulose in the pellicle is below 70%. For example, the crystallinity of the pellicle cellulose can be between about 50% and about 70%, or between about 55% and about 65%, or between about 60% and about 65%. In additional embodiments the crystallinity of the pellicle cellulose is about 45%, or about 50%, or about 55%, or about 60%, about 65% or about 68%.

In certain embodiments, product comprises live bacteria and fungi. In other embodiments, the product comprises killed bacteria and fungi. Cells in a pellicle can be killed by a variety of methods. These include, without limitation, boiling, high-pressure pasteurization, and exposure to UV radiation.

The pellicle can be removed from the fermentation vessel and cleaned, for example, by washing with water.

1. Product Nutrition

The co-culture of microorganisms food products of this disclosure have a protein (e.g., fungal protein) content of at least 5% protein by dry weight. For example, the products can have protein content of at least any of 6%, 7%, 8%, 9%, 10%, 11%, 12%, 13%, 14%, 15%, 16%, 17%, 18%, 19% or 20%, 25%, 30%, 35%, 40%, 45% or 50% protein by dry weight. In some embodiments, the product has at least 10% protein by dry weight.

The co-culture of microorganisms food products of this disclosure can have a fiber content of at least 5% fiber, e.g., cellulose, by dry weight. For example, the products can have fiber, e.g., cellulose content of at least any of 5%, 10%, 14%, 15%, 20%, 25%, 30%, 35%, 40%, 45%, 50%, 55%, or 60% fiber by dry weight. In some embodiments, fiber content is between about 5% and about 60%, between about 10% and about 50%, between about 15% and about 40%, between about 20% and about 40%, or between about 30% and about 40%.

In certain embodiments, the food products described herein are naturally high in fiber. The fiber content of food products can be determined using the AOAC method 991.43. (See, e.g., acnfp.food.gov.uk/sites/default/files/mnt/drupal_data/sources/files/multimedia/pdfs/annexg.pdf.)

Accordingly, certain products of this disclosure satisfy the FDA definition of high protein and high fiber. Pursuant to FDA 21 C.F.R. § 101.54, a product has a high nutrient content if the content is 20% or greater of the Recommended Daily Intake ("RDI") per reference amount customarily consumed (RACC). The RDI for protein is 50 g for adults and children aged 4 or older.

In some embodiments, the food products disclosed herein contain 10 g to 15 g protein per RACC (85 g) for entrees such as fish and shellfish. This is about 20-50% of the RDI, at least the amount to qualify as "high protein". In some embodiments, the product has at least any of 10 g, 11 g, 12 g, 13 g, 14 g, 15 g, 16 g, 17 g, 18 g, 19 g, or 20 g of protein per RACC for entrees such as fish and shellfish.

The RDI for dietary fiber is 28 g. In some embodiments, the food products disclosed herein can contain as much as 10 g to 14 g dietary fiber per RACC (85 g) for entrees such as fish and shellfish. This is about 35% to 50% of the RDI, greater than the amount to qualify as "high fiber". In some embodiments, the product has at least any of 10 g, 11 g, 12 g, 13 g, 14 g, 15 g, 16 g, 17 g, 18 g, 19 g, or 20 g of fiber per RACC for entrees such as fish and shellfish.

In some embodiments, the protein in the product comprises single-cell protein. The single-cell protein in the product can be derived substantially or solely from yeast and/or fungi. The protein can be a whole-protein, meaning that it has a protein digestibility amino acid score (PDCAAS) equal to at least any of 0.8, 0.85, 0.9, 0.95 or 1.0 e.g., equal to at least 0.9, e.g., 1.0.

2. Shaping the Product

A pellicle in the form of a slab of appropriate width, length and thickness can be formed into shapes that are attractive as food products. Typically, a single pellicle can be cut into a plurality of pieces having desired shapes. Shapes include, for example, discs, logs, strips, medallions, crescents, fans, rectangles, triangles, rings, slabs, etc. Pellicles can also be shaped as food products, for example, seafood products or poultry (e.g., chicken) products. Seafood product shapes include, for example, sushi, sashimi, shrimp, crab, lobster, squid/calamari. Shapes can include textures associated with the particular food product. Pellicles also can be shaped, for example as a chicken nugget, a bacon strip, a burger, or a sausage.

Forming into shapes can be accomplished by cutting or sculpting a pellicle. Cutting can be done with a cutting implement, for example, a knife, a wire, a cookie cutter, a die. A pellicle can be diced into pieces with a die. In another embodiment, a pellicle can be shaped by a mold during its formation. For example, a cover having shapes cut out of it can be placed on the surface of the culture medium on which a pellicle is forming. The pellicle will grow where the surface is exposed to oxygen, e.g., through the holes formed by the cut-out shapes, taking the shape of the hole. So, for example, a mold can comprise a plurality the same or different shape(s). Accordingly, a shaped product can be a product produced by a process of cutting or of molding.

Figure 4:
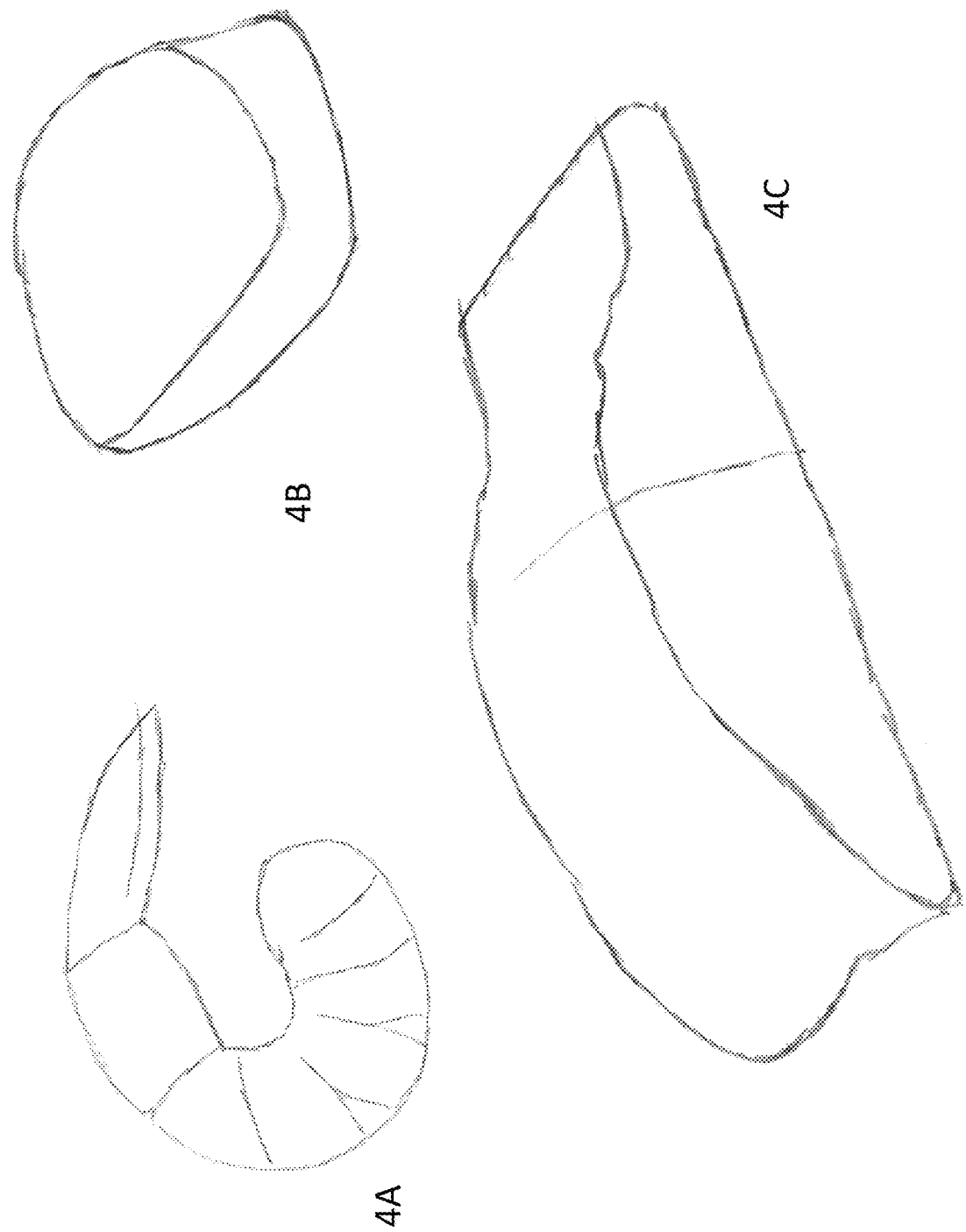
FIGS. 4A-4N depict exemplary food shapes made from pellicles.

FIGS. 4A-4N show exemplary shapes for food products made from pellicles. These include: shrimp (4A), scallop (4B), salmon steak (4C), calamari ring (4D), lobster claw (4E), crab claw (4F), calamari mantle (4G), sushi shapes (4H, 4I, 4J), nugget (4K), patty (4L), stick (e.g., fish stick) (4M), and bacon (4N).

3. Packaging

Food product pieces as described herein can be packaged in a container configured for shipping and transportation for example, an envelope, a bag, a box or a shipping tube. Packaging can include vacuum-sealing of the product in plastic. Packages can be refrigerated or frozen for later consumption.

III. Systems

FIG. 1 depicts a system configured to optimize growth and production of a co-culture of microorganisms, according to at least some embodiments disclosed herein. The system of FIG. 1 may be configured in a manner similar to a vertical garden using stacked trays. As described herein, a "vertical garden" is a system used to grow plants/fungi on a vertically suspended panel in stacked trays of depths between, e.g., 1 inches-50 inches, filled with a nutrient rich feedstock. Vertical gardens can be freestanding or attached to a wall. However, differing from the vertical garden technique, the system of FIG. 1 comprises a liquid feedstock, which will be discussed herein.

As shown in FIG. 1, the system comprises a housing unit 102 that includes stacked trays 104. Four stacked trays are depicted in FIG. 1. However, it should be appreciated that a quantity of the stacked trays is not limited to any particular quantity and four trays are being depicted for illustrative purposes only. The housing unit 102 is configured to maintain a temperature between approximately 40° F. and approximately 122° F. and is configured to maintain a relative humidity of approximately 20%-90% RH to facilitate growth of the fungus. In some examples, the preferred relative humidity is 90% RH. Each of the stacked trays 104 may be several inches deep. In some examples, each of the stacked trays 104 is up to 12 inches deep. However, this depth can vary.

As shown in FIG. 1, the stacked trays 104 may be vertically stacked. Further, each of the stacked trays 104 can be loosely covered to reduce evaporation rate and to allow oxygen to flow to the fermentation culture. Moreover, a gap exists between each tray of the stacked trays 104 to allow for heat and humidity transfer between the stacked trays 104. In some examples, this gap is up to 3 inches. However, the dimension of the gap can vary.

Each of the stacked trays 104 may serve as a fermentation vessel for the co-culture. For example, each of the stacked trays 104 may comprise a seed liquid inoculated with a starter culture. In examples, the seed liquid is a prepared broth comprising a feedstock. In examples, the feedstock comprises sugars and/or nitrogen sources and/or additional nutrients.

In some examples, the feedstock comprises glucose, fructose, sucrose, lactose, maltose, galactose, trehalose, allulose, honey, molasses, and/or maltotriose. In other examples, the culture medium comprises an infusion, that is, a composition comprising an ingredient, such as an herb, placed into a liquid (e.g., creating a tea). For example, the culture medium can comprise an infusion of *Camellia sinensis*, from which black tea, green tea, white tea, oolong tea, pu-erh tea, or purple tea may be harvested. In other examples, the feedstock comprises an infusion of *Ilex guayusa*, which is used to create yerba mate. In further examples, the culture medium can comprise an infusion of *Coffea arabica* or *Coffea robusta*. In another example, the culture medium comprises an infusion of an alga or seaweed, e.g., kelp. In certain embodiments a solid substance such as tea leaves or ground coffee beans can be added to the fermentation culture, such that the culture itself is an infusion of the added substance. In additional embodiments, a liquid infusion of a solid substance, e.g., liquid tea or coffee, is added to the fermentation culture.

However, it should be appreciated that the culture medium or feedstock are not limited to such. Under aerobic conditions, sugars and nutrients are fermented in the presence of a culture or co-culture of microorganisms. In some examples, a high concentration of the liquid culture added to the feedstock optimizes growth of the fungus. In examples, this high concentration results in approximately 50%-99% of the maximum growth rate of the fungi.

Once the seed liquid is prepared, the seed liquid may be used as a base for an active fermentation process to form a microbial consortium. Moreover, the microbiomes may colonize the dissolved substrate cultivating the consortium material via submerged fermentation or surface fermentation. As described herein, "submerged fermentation" refers to a method of manufacturing biomolecules in which microorganisms, enzymes and other reactive compounds are submerged in a liquid, such as alcohol, oil, or a nutrient broth; while "surface fermentation" refers to a process in which microorganisms reside on the surface of a liquid (e.g., as a pellicle). Further, a complex of organic acids, exopolysaccharides and enzymes is produced during fermentation.

As described herein, the product comprises a co-culture of bacteria and fungi. The exact microbial composition of the product depends on the source of the inoculum for the fermentation.

In certain embodiments, the co-culture of microorganisms comprises the fungus *Medusomyces gisevii* Lindau. It should be appreciated that the fungus is not limited to the examples provided herein. Additionally, the fermentation culture may include: yeast, bacteria, nutrients, probiotics, microbes, a vinegar by-product of an aerobic digestion of a sugar (e.g., glucose) and nitrogen, and/or prebiotics, among other components not explicitly listed herein. According to some examples, the bacterium comprises a genus of *Acetobacter* or *Gluconobacter*. The predominant acetic acid bacteria found in the tea fungus comprises *A. xylium, A. pasteurianus, A. aceti*, or *Gluconobacter oxydans*. The yeast may include species of *Saccharomyces, Saccharomycodes, Schizosaccharomyces, Zygosaccharomyces, Brettanomyces/Dekkera, Candida, Torulaspora, Koleckera, Pichia, Mycotorula*, or *Mycoderma*. Moreover, in certain embodiments, the fermentation culture includes a biomass material (e.g., pieces of the same fungi that are grown from a previous batch) configured to accelerate a growth of the fungus.

The material produced by the system of FIG. 1 may be used in numerous applications. In preferred examples, the material (e.g., pellicle) is used in a food application, such as a source of food, as a protein source, or is used in applications of plant protein products, including meat, seafood and poultry analogues.

Figure 2:
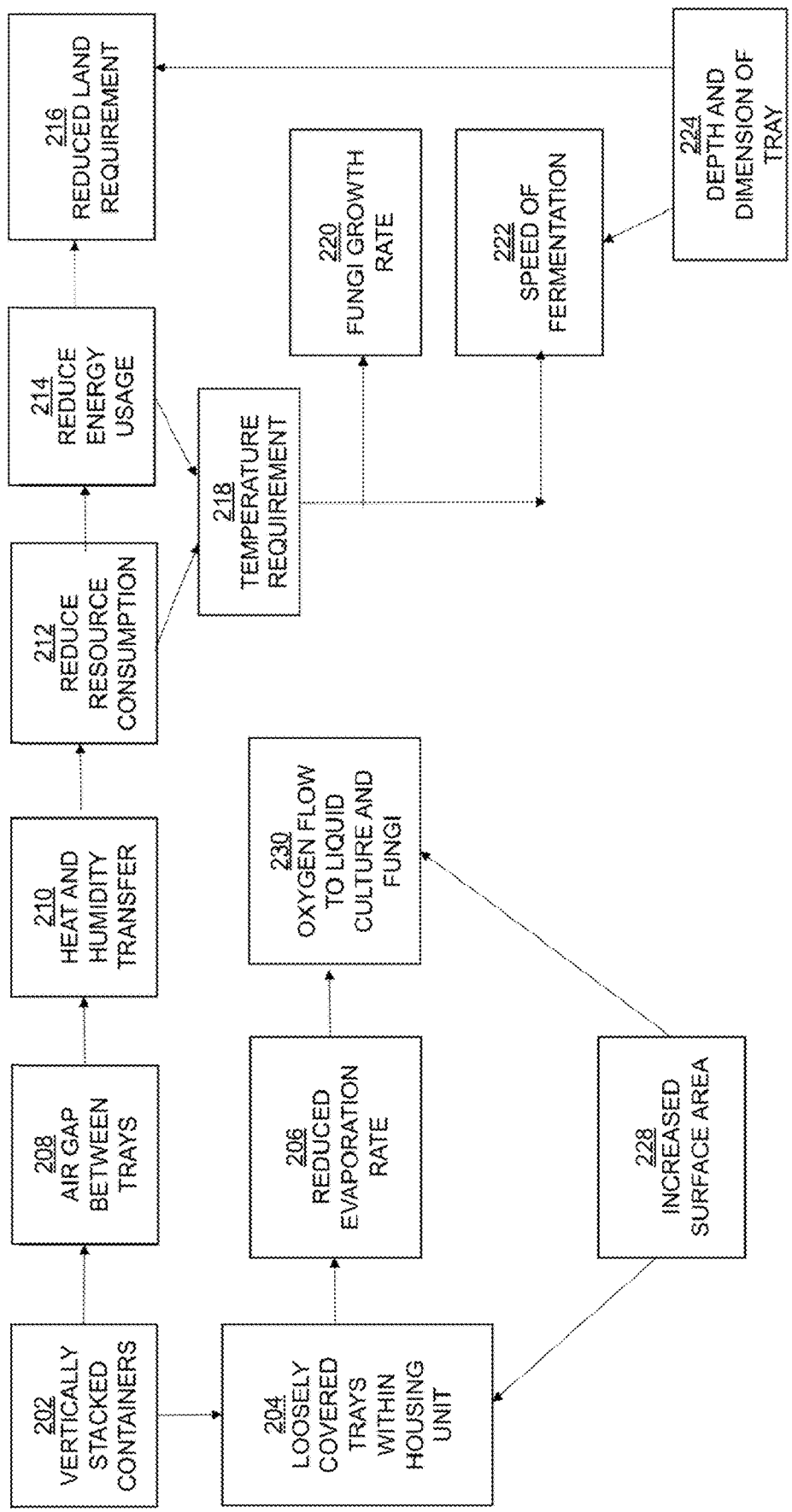
FIG. 2 depicts a block diagram of a system, according to at least some embodiments disclosed herein.

FIG. 2 depicts a block diagram of a system, according to at least some embodiments disclosed herein. As shown in FIG. 2, the system includes vertically stacked containers 202 that comprise loosely covered trays within a housing unit 204. The trays have an increased surface area 228. An air gap exists between the trays 208 such that heat and humidity can be transferred 210, which also reduces resource consumption 212, reduces energy usage 214, and reduces land requirements 216. Maintenance of temperature and humidity contributes to the growth of the co-culture. In some examples, the preferred relative humidity is approximately 20% to 90% RH. In some examples, the preferred relative humidity is 90% RH. However, this example is provided for illustrative purposes only. The loosely covered trays within the housing unit 204 help reduce evaporation rate 206 and allow oxygen to flow to the liquid culture and fungi 230. However, the cover is not necessary. Both the temperature requirement 218 for the system and the depth and dimension of the tray 224 influence the growth rate of fungi in the co-culture 220 and the speed of the fermentation 222.

EXEMPLARY EMBODIMENTS

1. A composition comprising a solid product of a co-culture of bacteria and fungi, comprising at least 5% protein by dry weight and at least 5% fiber by dry weight.

2. The composition of embodiment 1, wherein the food product comprises a scaffold comprising cellulose.

3. The composition of embodiment 1, comprising killed bacteria and fungi and/or live bacteria and fungi.

4. The composition of embodiment 1, wherein the composition is high protein and high fiber.

5. The composition of embodiment 1, comprising at least any of 6%, 7%, 8%, 9%, 10%, 15%, 20%, 25%, 30%, 35%, 40%, 45% or 50% fungal protein by dry weight.

6. The composition of embodiment 1, wherein a majority of the protein is a mycoprotein.

7. The composition of embodiment 1, wherein the protein has a digestibility amino acid score (PDCAAS) equal to at least any of 0.8, 0.85, 0.9, 0.95 or 1.0.

8. The composition of embodiment 1, wherein the composition comprises at least any of 5%, 10%, 15%, 20%, 25%, 30%, 35%, 40%, 45% or 50% bacterial fiber by dry weight.

9. The composition of embodiment 8, wherein the bacterial fiber comprises bacterial cellulose.

10. The composition of embodiment 1, wherein the fiber comprises chitin.

11. The composition of embodiment 1, wherein at least 15% of the fiber comprises fungal fiber.

12. The composition of embodiment 1, wherein the fungi proliferate in an acidic pH environment and have a low flocculation rate.

13. The composition of embodiment 1, wherein the fungi comprise yeast that are not strong fermenters.

14. The composition of embodiment 1, wherein the fungi comprise filamentous fungi.

15. The composition of embodiment 1, wherein the fungi are selected from *Aspergillus* (e.g., *Aspergillus oryzae*), *Fusarium* (e.g., *Fusarium venenatum*), tea fungus (e.g., *Medusomyces gisevii* Lindau), *Geotrichum* (e.g., *Geotrichum candidum*), *Penicillium* (e.g., *Penicillium camemberti* or *Penicillium roqueforti*), *Neurospora* (e.g., *Neurospora crassa*), *Paecilomyces* (e.g., *Paecilomyces variotii*) and *Rhizopus* ((e.g., *Rhizopus oligosporus*).

16. The composition of embodiment 1, wherein the fungus is selected from *Candida* (e.g., *Candida utilis*), *Rhodotorula* (e.g., *Rhodotorula mucilaginosa*), *Cyberlindnera* (e.g. *Cyberlindnera jadinii*), and *Pichia* (e.g., *Pichia pastoris*).

17. The composition of embodiment 1, wherein the fungi comprise filamentous fungi.

18. The composition of embodiment 1, wherein the bacterium is selected from a genus selected from *Gluconacetobacter, Acetobacter, Komagataeibacter* and *Gluconobacter*.

19. The composition of embodiment 1, comprising whole bacterial cells and/or whole fungal cells.

20. The composition of embodiment 1, comprising a bacterium selected from *Gluconacetobacter* and *Komagataeibacter*, and a fungus selected from *Candida* and *Aspergillus*.

21. The composition of embodiment 1, comprising *Gluconacetobacter* and *Aspergillus*.

22. The composition of embodiment 1, comprising a pair of a bacterium and a fungus selected from Table 1.

23. The composition of embodiment 1, formed into a shape by cutting or molding.

24. A food composition or food article comprising fungal cells embedded in a scaffold comprising cellulose (e.g., bacterial cellulose), and comprising a protein content of at least 5% by dry weight and a fiber content of at least 5% by dry weight.

25. The food composition or food article of embodiment 24, further comprising bacterial cells embedded in the scaffold.

26. A food article formed from a pellicle formed as a product of a co-culture of bacteria and fungi, which comprises at least 5% fungal protein by dry weight and at least 5% fiber by dry weight, and which is formed into a shape by cutting or molding.

27. The article of embodiment 26, comprising a scaffold comprising cellulose, wherein bacteria and fungi are embedded in the scaffold.

28. The article of embodiment 26, comprising killed bacteria and fungi and/or living bacteria and fungi.

29. The article of embodiment 26, formed in the shape of a strip, a ring, a disk, a log, a crescent, a fan, a rectangle, a triangle, a medallion, or a slab.

30. The article of embodiment 26, formed in the shape of a seafood product.

31. The article of embodiment 30, wherein the seafood is selected from a cephalopod, crustacean or a bony fish (e.g., shrimp, sushi, sashimi, crab, lobster, squid/calamari).

32. The article of embodiment 26, wherein the product is in the shape of a patty (e.g., burger) or nugget (e.g., chicken nugget).

33. The article of embodiment 26, wherein the product is configured as a piece having a rectangular shape and a surface area of at least 150 cm2.

34. The article of embodiment 26, having a volume no greater than any of 1000 cm3, 729 cm3, 512 cm3, 343 cm3, 216 cm3, 125 cm3, 64 cm3, 27 cm3, 8 cm3, or 1 cm3.

35. The article of embodiment 34, having a volume at least 1 cm$^3$.

36. The article of embodiment 26, wherein the product has a cutting force less than about 3 kilogram-force, a density of about 0.2 to about 1.5 grams per cm3, and a water content of about 50% to about 75% by weight.

37. The article of embodiment 26, comprising at least 14% fungal protein and at least 14% bacterial cellulose by dry weight.

38. A method of making a food product comprising a co-culture of bacteria and fungi, comprising:
  (a) combining, in a fermentation vessel, a starter culture and a culture medium, to produce a culture, wherein:
    (i) the starter culture comprises one or more fungi and one or more cellulose-producing bacteria; and
    (ii) the culture medium comprises water, a carbon source, a nitrogen source, and nutrients; and
    (iii) the fermentation vessel has a volume-to-surface area ratio of at least 3:1; and
  (b) incubating the culture for a time sufficient to produce a pellicle, wherein the pellicle comprises at least 5% fungal protein by dry weight and at least 5% fiber by dry weight.

39. The method of embodiment 38, further comprising:
  (c) harvesting the pellicle.

40. The method of embodiment 38 or 39, further comprising killing bacteria or fungi in the pellicle, e.g., by boiling, pasteurizing or irradiating.

41. The method of embodiment 38, wherein the product is high protein and high fiber.

42. The method of embodiment 38, wherein the bacteria do not comprise lactic acid bacteria or an agricultural substrate.

43. The method of embodiment 38, wherein the fungi are present, in the starter culture, at an amount at least 3% of wet weight.

44. The method of embodiment 38, wherein the bacteria are present in the starter culture at an amount at least any of 1%, at least 2%, at least 5%, at least 10% of wet weight.

45. The method of embodiment 38, wherein the culture medium comprises one or more of glucose, fructose, peptone (animal or plant based), yeast extract, disodium phosphate, magnesium sulfate heptahydrate, and potassium hydrogen phosphate.

46. The method of embodiment 38, wherein the carbon source comprises one or more of: glucose, fructose, sucrose, lactose, maltose, galactose, trehalose, allulose, maltotriose, honey and molasses.

47. The method of embodiment 38, wherein the carbon source comprises a non-sugar carbon source.

48. The method of embodiment 38, wherein the carbon source comprises one or more of: ethanol, methanol, sorbitol, mannitol, xanthan, agar, alginate, and konjac glucomannan.

49. The method of embodiment 38, wherein the nitrogen source is present in an amount of at least 5 grams per liter, at least 7.5 grams per liter, at least 10 grams per liter or at least 15 grams per liter.

50. The method of embodiment 38, wherein the nitrogen source is an organic nitrogen source, and the organic nitrogen source is present in an amount of at least 5 grams per liter.

51. The method of embodiment 38, wherein the organic nitrogen source is present in the culture medium in an amount of at least 0.5% by weight.

52. The method of embodiment 38, wherein the organic nitrogen source comprises amino acids, polypeptides, nucleotides or nucleic acids.

53. The method of embodiment 51, wherein the organic nitrogen source comprises a yeast extract, a peptone, or an agricultural product comprising amino acids (e.g., a hydrolyzed corn protein, a hydrolyzed soy protein, a hydrolyzed pea protein, and a corn steep liquor).

54. The method of embodiment 38, wherein the nitrogen source is an inorganic nitrogen source, e.g., a nitrate salt, an ammonia salt, a urea compound, nitrogen gas, and ammonium hydroxide.

55. The method of embodiment 38, wherein the fermentation culture comprises yeast, bacteria, nutrients, probiotics, microbes, a vinegar by-product of an aerobic digestion of sugar and nitrogen, and/or a prebiotic.

56. The method of embodiment 38, wherein the fermentation culture has a volume of at least any of 100 ml, 250 ml, 500 ml, 1 liter, 2 liters, 5 liters or 10 liters.

57. The method of embodiment 38, wherein the fermentation vessel comprises a tray having a surface area of at least 400 cm2 and a depth of at least 2 cm2.

58. The method of embodiment 38, wherein the fermentation vessel comprises a tray having a surface area of at least 400 cm2 and a depth of at least 2 cm, e.g., having a surface area of at least 600 cm2 and a depth of at least 3 cm.

59. The method of embodiment 38, wherein fermenting comprises aerating the fermentation culture.

60. The method of embodiment 58, wherein aeration is performed by providing air with an air pump.

61. The method of embodiment 38, comprising fermenting in an open fermentation vessel.

62. The method of embodiment 38, wherein the tray is covered with a porous material, e.g., cheese cloth.

63. The method of embodiment 38, wherein the tray is covered to reduce but not eliminate evaporation, and to allow oxygen to flow to the fermentation culture.

64. The method of embodiment 38, comprising fermenting for 5 days to 25 days.

65. The method of embodiment 38, wherein fermenting comprises maintaining temperature between about 40° F. to about 122° F., e.g., between about 50° F. to about 90° F., between about 60° F. to about 80° F., between about 65° F. to about 75° F., or about 68° F.

66. The method of embodiment 38, wherein the fermentation culture is started at pH around 4.5.

67. The method of embodiment 38, wherein the fermentation culture is maintained between about pH 4.0 and about pH 5.0, e.g., about pH 4.5.

68. The method of embodiment 38, wherein fermenting comprises maintaining humidity between 20% and 90% RH, e.g., between 40% and 60% RH or about 50% RH.

69. The method of embodiment 38, comprising covering the fermentation vessel with a cover comprising one or a plurality of apertures having one or a plurality of shapes, wherein the pellicle forms in the apertures and takes the shape of the apertures.

70. The method of embodiment 69, wherein a plurality of fermentation vessels are stacked on top of each other.

71. The method of embodiment 38, wherein harvesting the pellicle comprises removing the pellicle from the fermentation vessel and washing the pellicle.

72. The method of embodiment 71, further comprising subjecting the pellicle to boiling, pasteurization, high pressure or irradiation.

73. The method of embodiment 38, wherein the product has a cutting force that is less than 5 kilogram-force.

74. A method of making a food product comprising:
(a) providing a pellicle which is the product of a co-culture of bacteria and fungi; and
(b) shaping the pellicle into a plurality of pieces.

75. The method of embodiment 74, further comprising:
(c) cutting the product into a plurality of pieces, wherein the pieces have shapes selected from strip, a ring, a disk, a log, a crescent, a fan, a rectangle, a triangle, a medallion, or a slab.

76. The method of embodiment 74, further comprising:
(c) cutting the product into a plurality of pieces, wherein the pieces have shapes selected from shrimp, sushi, sashimi, crab, lobster, squid/calamari, patties, or nuggets.

77. The method of embodiment 74, wherein the pellicle has a thickness of at least about any of 1 cm, 2 cm, 3 cm, 4 cm, 5 cm, or 10 cm.

78. The method of embodiment 74, wherein the pellicle comprises at least 5% protein and at least 5% fiber by dry weight.

79. A system comprising:
a) an incubator comprising an incubator space;
b) a temperature regulator configured to control temperature in the incubator space;
c) a humidifier configured to control humidity within the incubator space;
d) inside the incubator space, at least one tray having a culture wherein the culture has a volume-to-surface area ratio of at least 3:1 wherein the culture comprises a co-culture of bacteria and fungi.

80. The system of embodiment 79, further comprising an air source that delivers air to the culture.

81. A system to optimize a growth and a production of a co-culture that forms a product comprising a high-protein, high-fiber material, the system comprising: a housing unit comprising stacked trays housing a seed liquid inoculated with a starter culture.

82. The system of embodiment 81, wherein the seed liquid is a prepared broth comprising a feedstock.

83. The system of embodiment 81, wherein the feedstock comprises sugars and nutrients.

84. The system of embodiment 83, wherein the sugars are selected from the group consisting of: glucose, fructose, sucrose, lactose, galactose, maltose, trehalose, allulose, and maltotriose.

85. The system of embodiment 83, wherein the nutrients are selected from the group consisting of honey and molasses.

86. The system of embodiment 81, wherein the feedstock comprises infused *Camellia sinensis*, infused *Ilex guayusa*, infused *Coffea arabica*, or infused *Coffea robusta*.

87. The system of embodiment 81, wherein each of the stacked trays are loosely covered to reduce an evaporation rate and to allow oxygen to flow to the seed liquid and the fungus.

88. The system of embodiment 81, wherein a gap exists between each tray of the stacked trays to allow for heat and humidity transfer between the stacked trays.

89. The system of embodiment 81, wherein the fungus comprises a tea fungus.

90. The system of embodiment 89, wherein the tea fungus comprises *Medusomyces gisevii* Lindau.

91. The system of embodiment 81, wherein the fungus is used in a food application.

92. The system of embodiment 91,
wherein the fungus is used in the food application, and
wherein the food application comprises a food source or a protein source.

93. The system of embodiment 92, wherein the food application is selected from the group consisting of: an alternative protein, a plant-based meat product, a plant-based seafood product, a plant-based poultry product, a dairy analogue product, a beverage product, a breakfast cereal product, a grain product, a baking mix, a soup mix, a fat, and an oil.

94. The system of embodiment 81, wherein the stacked trays are stacked vertically to allow for a maintenance of temperature and humidity.

95. The system of embodiment 94, wherein the temperature is maintained between approximately 40° F. to approximately 122° F.

96. The system of embodiment 94, wherein the humidity is maintained between 20-90% RH.

97. The system of embodiment 96, wherein the humidity is maintained at 90% RH.

98. The system of embodiment 81, wherein the fermentation culture comprises fungi, bacteria, nutrients, probiotics, microbes, a vinegar by-product of an aerobic digestion of glucose and nitrogen, and/or prebiotics.

EXAMPLES

A pellicle comprising a symbiotic co-culture of bacteria and fungi is prepared as follows:
Materials and Methods
All materials are food grade and generally regarded as safe (GRAS) in the concentrations that they are used.
The following describes a method for making 1L of culture media:

Mixture 1
35 g glucose
25 g fructose
500 mL of 100 mM acetate buffer in distilled water, pH=4.6

Components are stirred to dissolve and autoclaved at 121° C. for 20 minutes.

Mixture 2
2.5-7.5 g yeast extract, peptone, amino acids
2 mL v/v ethanol (optional)
5 g $KH_2PO_4$,
2 g $NH_4NO_3$
0.2 g $MgSO_4$ 1 g $CaSO_4$
0.005 g $Zn\ SO_4$
0.001 g $Fe(NH_4)_2(SO_4)2$ 0.00025 g $CuSO_4$ 0.0001 g $MnSO_4$
0.0025 g biotin
500 mL of 100 mM acetate buffer in distilled water, pH=4.6

Components are stirred to dissolve and autoclaved at 121° C. for 20 minutes.

Combine Mixture 1 and 2 to produce 1 L of culture medium.

Fermentation Culture 500 mL of culture medium is added to an autoclaved rectangular polycarbonate tray with dimensions: 40×132×145 mm. The surface area to volume ratio of the media in the tray is 0.25 to 0.30 $cm^{-1}$. The culture medium is aerated to have a measured dissolved oxygen content of 6-8 mg/L. To a flask, 1 inoculation loop of *Komagataeibacter xylinus* and 1 inoculation loop of *Aspergillus oryzae* are aseptically transferred. The seed inoculum is added to the tray. A cover allowing for gas exchange is placed over the opening of the tray.

The contents are left to proliferate statically in an incubator at 27.5° C. and 60% RH for 4-30 days. After 4 days, a translucent, white pellicle, having a thickness of approximately 1-2 mm, begins to form on the surface of the culture medium. After 14 days, the pellicle becomes more opaque and white and can have a thickness ranging from 10-20 mm. The evaporation rate of the culture medium is about 2-5 mL of water per day. The pellicle is typically 60% water, 14-20% fiber and 14-20% protein; the remaining material comprising organic acids, residual carbohydrates, minerals and vitamins, such as Vitamin B6, B12, folic acid, thiamine, riboflavin, niacin, iron, copper and zinc.

After a desired time, the pellicle is removed from the culture medium, rinsed in distilled water until the pH is stable at pH=6-7. and stored at 4° C. in distilled water until further processing into a food product. Optionally, the pellicle is subjected to boiling, autoclaving, increased pressure (e.g., 2, 3, 4, or 5 atmospheres) and/or irradiation (e.g. ultraviolet irradiation) prior to processing.

As used herein, the following meanings apply unless otherwise specified. The words "can" and "may" are used in a permissive sense (i.e., meaning having the potential to), rather than the mandatory sense (i.e., meaning must). The words "include", "including", and "includes" and the like mean including, but not limited to. The singular forms "a," "an," and "the" include plural referents. Thus, for example, reference to "an element" includes a combination of two or more elements, notwithstanding use of other terms and phrases for one or more elements, such as "one or more." The phrase "at least one" includes "one", "one or more", "one or a plurality", and, therefore, contemplates the use of the term "a plurality". The term "or" is, unless indicated otherwise, non-exclusive, i.e., encompassing both "and" and "or." The term "any of" between a modifier and a sequence means that the modifier modifies each member of the sequence. So, for example, the phrase "at least any of 1, 2 or 3" means "at least 1, at least 2 or at least 3". The term "about" refers to a range that is 5% plus or minus from a stated numerical value within the context of the particular usage. The term "consisting essentially of" refers to the inclusion of recited elements and other elements that do not materially affect the basic and novel characteristics of a claimed combination.

It should be understood that the description and the drawings are not intended to limit the invention to the particular form disclosed, but to the contrary, the intention is to cover all modifications, equivalents, and alternatives falling within the spirit and scope of the present invention as defined by the appended claims. Further modifications and alternative embodiments of various aspects of the invention will be apparent to those skilled in the art in view of this description. Accordingly, this description and the drawings are to be construed as illustrative only and are for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims.

All publications, patents, and patent applications mentioned in this specification are herein incorporated by reference to the same extent as if each individual publication, patent, or patent application was specifically and individually indicated to be incorporated by reference.

What is claimed is:

1. A method of producing an edible pellicle comprising:
   (a) preparing a fermentation culture by combining, in a fermentation vessel:
      (i) one or more filamentous fungi;
      (ii) one or more cellulose-producing bacteria; and
      (iii) a culture medium comprising water, a carbon source, a nitrogen source, and nutrients;
   (b) incubating the culture under culture conditions for a time sufficient to produce a pellicle comprising a bacterial cellulose scaffold and fungi mycelia embedded in the scaffold, wherein the pellicle comprises at least 5% fungal protein by dry weight and at least 5% fiber by dry weight;
   (c) killing the bacteria and fungi in the pellicle to produce an edible pellicle; and
   (d) harvesting the edible pellicle, wherein the edible pellicle is not dehydrated.

2. The method of claim 1, further comprising:
   (e) cutting the edible pellicle into a plurality of shapes or minced pieces.

3. The method of claim 2, wherein the shapes are selected from a strip, a ring, a disk, a log, a crescent, a fan, a rectangle, a triangle, a medallion, a slab, and combinations thereof.

4. The method of claim 2, wherein the edible pellicle is processed to mimic a shrimp, crab claw, lobster claw, scallop, tuna, squid/calamari mantle, patty, or nugget.

5. The method of claim 1, wherein the fermentation culture is maintained between about pH 4.0 and about pH 5.0.

6. The method of claim 1, wherein killing comprises subjecting the pellicle to boiling, pasteurization, high pressure or irradiation.

7. The method of claim 1, wherein the fermentation culture is started at pH around 4.5.

8. The method of claim 1, wherein the one or more bacteria comprise one or more of *Komagataeibacter, Acetobacter*, and *Gluconacetobacter*.

9. The method of claim 8, wherein the one or more fungi comprise one or more of *Aspergillus, Neurospora,* and *Fusarium*.

10. The method of claim 1, wherein the one or more fungi comprise one or more of *Aspergillus, Neurospora,* and *Fusarium*.

11. The method of claim 1, wherein the culture comprises *Komagataeibacter* and *Aspergillus*.

12. The method of claim 1, wherein the bacteria do not comprise lactic acid bacteria.

13. The method of claim 1, wherein the carbon source comprises one or more sugars.

14. The method of claim 1, wherein the nitrogen source is present at a concentration of at least 5 g/liter.

15. The method of claim 1, wherein the nitrogen source comprises an organic nitrogen source.

16. The method of claim 15, wherein the organic nitrogen source comprises amino acids, polypeptides.

17. The method of claim 15, wherein the organic nitrogen source comprises a yeast extract, a peptone, a hydrolyzed corn protein, a hydrolyzed soy protein, a hydrolyzed pea protein, or a corn steep liquor.

18. The method of claim 1, wherein the nitrogen source comprises an inorganic nitrogen source.

19. The method of claim 1, wherein the fermentation culture comprises the carbon source at a concentration of at least 10 g/liter; the nitrogen source at a concentration of at least 2 g/liter; and wherein the nutrients comprise salts of magnesium, iron and copper.

20. The method of claim 1, wherein the fermentation culture does not comprise an agricultural substrate.

21. The method of claim 1, wherein incubating comprises aerating the fermentation culture.

22. The method of claim 1, wherein the fermentation culture has a volume of at least 5 liters.

23. The method of claim 1, wherein the fermentation culture has a volume of at least 10 liters.

24. The method of claim 1, wherein the fermentation vessel has a surface area-to-volume ratio of between about 1:4 and about 1:6.

25. The method of claim 1, wherein the fermentation vessel comprises a tray having a surface area of at least 400 $cm^2$ and a depth of at least 2 $cm^2$.

26. The method of claim 1, comprising incubating for 5 days to 25 days.

27. The method of claim 1, comprising covering the fermentation vessel with a cover comprising one or a plurality of apertures having one or a plurality of shapes, wherein the pellicle forms in the apertures and takes the shape of the apertures.

28. The method of claim 1, comprising growing the pellicle to a thickness of at least about 5 mm.

29. The method of claim 1, wherein the pellicle comprises at least 10% fungal protein by dry weight and at least 10% fiber by dry weight.

30. The method of claim 1, wherein the edible pellicle comprises a water content of about 50% to about 75% by weight.

* * * * *